United States Patent
Ahmed et al.

(10) Patent No.: US 11,131,660 B2
(45) Date of Patent: Sep. 28, 2021

(54) METHOD AND APPARATUS TO MEASURE WATER CONTENT OF PETROLEUM FLUIDS

(71) Applicant: Saudi Arabian Oil Company, Dhahran (SA)

(72) Inventors: Elaf A. Ahmed, Dhahran (SA); Sebastien A. Duval, Dhahran (SA); Simone Less, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 225 days.

(21) Appl. No.: 16/575,082

(22) Filed: Sep. 18, 2019

(65) Prior Publication Data

US 2021/0080446 A1 Mar. 18, 2021

(51) Int. Cl.
*G01N 33/18* (2006.01)
*G01N 33/28* (2006.01)

(52) U.S. Cl.
CPC .................. *G01N 33/2847* (2013.01)

(58) Field of Classification Search
CPC ............... G01N 33/18; G01N 33/2847
USPC .............................................. 436/40
See application file for complete search history.

(56) References Cited

U.S. PATENT DOCUMENTS

| | | | | |
|---|---|---|---|---|
| 2,758,477 A | * | 8/1956 | Haeber | G01N 9/26 73/438 |
| 3,133,437 A | * | 5/1964 | Remke | G01N 27/223 73/61.44 |
| 3,222,918 A | * | 12/1965 | Kuntz | G01N 33/2823 73/53.01 |
| 3,462,596 A | * | 8/1969 | Saunders | G01N 21/3577 250/304 |
| 3,528,775 A | * | 9/1970 | Siegfriedt | G01N 31/168 436/40 |
| 3,539,917 A | * | 11/1970 | Chleck | G01N 27/121 422/88 |
| 3,546,926 A | * | 12/1970 | Scott | G01N 27/223 73/61.43 |

(Continued)

FOREIGN PATENT DOCUMENTS

| | | |
|---|---|---|
| CN | 105974098 | 9/2016 |
| DE | 102004010650 | * 9/2005 |

(Continued)

OTHER PUBLICATIONS

Delfino, J. R. et al, Taianta 2018, 179, 753-759.*

(Continued)

*Primary Examiner* — Arlen Soderquist
(74) *Attorney, Agent, or Firm* — Fish & Richardson P.C.

(57) ABSTRACT

To measure above-saturation water content of hydrocarbons, a liquid hydrocarbon sample is received from a flowline carrying the liquid hydrocarbon. The liquid hydrocarbon sample includes liquid hydrocarbon and liquid water at a concentration greater than a water saturation level. The liquid hydrocarbon sample is mixed with a solvent. The concentration of liquid water in a mixture of the solvent and the liquid hydrocarbon sample is below the water saturation level. After mixing the liquid hydrocarbon sample with the solvent, a water content in the liquid hydrocarbon sample is determined.

18 Claims, 2 Drawing Sheets

(56) References Cited

U.S. PATENT DOCUMENTS

| | | | |
|---|---|---|---|
| 3,553,576 A * | 1/1971 | Petitjean | G01N 27/121 |
| | | | 324/695 |
| 3,727,049 A | 4/1973 | Saunders | |
| 4,301,400 A * | 11/1981 | Paap | G01R 27/04 |
| | | | 324/601 |
| 5,067,345 A | 11/1991 | Mougne | |
| 5,187,101 A * | 2/1993 | Kato | G01N 31/168 |
| | | | 436/42 |
| 5,259,239 A | 11/1993 | Gaisford | |
| 7,469,188 B2 | 12/2008 | Wee | |
| 8,323,392 B2 | 12/2012 | Jones et al. | |
| 9,448,221 B2 | 9/2016 | Duval et al. | |
| 2006/0186340 A1 * | 8/2006 | Lievois | G01N 21/3554 |
| | | | 250/339.12 |
| 2006/0286675 A1 * | 12/2006 | Coleman | G01N 33/2852 |
| | | | 436/143 |
| 2011/0194105 A1 | 8/2011 | LaFrancois et al. | |
| 2013/0110411 A1 | 5/2013 | Black et al. | |
| 2013/0277551 A1 | 10/2013 | Bourrel et al. | |
| 2018/0031524 A1 * | 2/2018 | Hassell, Jr. | G01N 29/024 |

FOREIGN PATENT DOCUMENTS

| | | | |
|---|---|---|---|
| JP | S 6140555 | | 2/1986 |
| SU | 1183890 | * | 10/1985 |

OTHER PUBLICATIONS

Glasoe et al, "Solubility of water and deuterium oxide in carbon tetrachloride, toluene, and cyclohexane at various temperatures," Journal of Chemical & Engineering Data, 17(1), pp. 66-68, 1972, 3 pages.

Johnson et al, "The Molecular Complexity of Water in Organic Solvents Part II," J. Chem. Soc. A, Inorganic Phys. Theoretical, pp. 77-78, 1966, 2 pages.

Kirchnerová et al, "The Solubility of Water in Low-Dielectric Solvents," Can. J. Chem 54(24), pp. 3909-3916, Aug. 26, 1976, 8 pages.

Knauss et al, "The solubility of p-xylene in water as a function of temperature and pressure and calculated thermodynamic quantities," Geochimica et Cosmochimica Acta vol. 59, Issue 12, Jun. 1995, pp. 2443-2448, Mar. 1995, 6 pages.

Michell Instruments, "Impedance," Impedance Products, URL: <http://www.michell.com/uk/technology/impedence.htm> retrieved Sep. 9, 2019, 2 pages.

Odberg et al, "Studies of water in organic solvents using NMR and partition techniques-II Di-isopropyl ether, dibutyl phthalate and chloroform," Journal of Inorganic and Nuclear Chemistry vol. 34, Issue 8, Aug. 1972, pp. 2605-2616, Mar. 18, 1971, 12 pages.

Sensorland.com, "Impedance Moisture Sensor Technology," How Sensors work—Moisture Sensors, URL: <http://www.sensorland.com/HowPage029.html> retrieved Sep. 9, 2019, 2 pages.

Vaisala, "Vaisala HUMICAP Sensor for Measuring Moisture in Oil," Technology Description, URL: <https://www.vaisala.com/sites/default/files/documents/HUMICAP-for-Moisture-in-oil-B211231EN-A.pdf> 2012, 2 pages.

PCT International Search Report and Written Opinion in International Appln. No. PCT/US2020/051227, dated Jan. 28, 2021, 15 pages.

Karma et al., "Estimating the Amount of Moisture Content in Crude Oil Samples," International Refereed Journal of Engineering and Science (IRJES), Feb. 2017, 6(2): 59-62, 4 pages.

* cited by examiner

US 11,131,660 B2

METHOD AND APPARATUS TO MEASURE WATER CONTENT OF PETROLEUM FLUIDS

TECHNICAL FIELD

This disclosure relates to measuring water content of hydrocarbons, for example, petroleum fluids.

BACKGROUND

Hydrocarbon produced from subsurface reservoirs through wellbores can include petroleum, water, natural gas or combinations of them. Water cut is defined as the ratio of a volume of water produced to a volume of total liquids produced through the wellbore. Water cut above a certain water cut threshold can result in inefficiencies in the processing, for example, refining, of the hydrocarbons.

SUMMARY

This disclosure describes technologies relating to measuring above-saturation water content of hydrocarbons.

Certain aspects of the subject matter described here can be implemented as a method. A liquid hydrocarbon sample is received from a flowline carrying the liquid hydrocarbon. The liquid hydrocarbon sample includes liquid hydrocarbon and liquid water at a concentration greater than a water saturation level. The liquid hydrocarbon sample is mixed with a solvent. The concentration of liquid water in a mixture of the solvent and the liquid hydrocarbon sample is below the water saturation level. After mixing the liquid hydrocarbon sample with the solvent, a water content in the liquid hydrocarbon sample is determined.

An aspect combinable with any of the other aspects includes the following features. The liquid hydrocarbon sample is flowed into a measurement cell.

An aspect combinable with any of the other aspects includes the following features. A temperature of the measurement cell is controlled to remain substantially at a temperature before mixing the liquid hydrocarbon sample with the solvent and during determining the water content of the liquid water in the liquid hydrocarbon sample.

An aspect combinable with any of the other aspects includes the following features. The temperature is 40° C.

An aspect combinable with any of the other aspects includes the following features. To mix the liquid hydrocarbon sample with a solvent, the solvent is flowed into the measurement cell.

An aspect combinable with any of the other aspects includes the following features. Before mixing the liquid hydrocarbon sample with the solvent, it is determined that a water content of the solvent is greater than a water content threshold. Responsively, an alarm signal is transmitted to cease mixing the liquid hydrocarbon sample with the solvent.

An aspect combinable with any of the other aspects includes the following features. The water content is transmitted to a computer system. The water content is displayed on a display device connected to the computer system.

An aspect combinable with any of the other aspects includes the following features. The mixture of the solvent and the liquid hydrocarbon sample is flowed to the flowline.

An aspect combinable with any of the other aspects includes the following features. The liquid hydrocarbon sample is a first liquid hydrocarbon sample, the solvent is a first solvent, and the water content is a first water content. The first water content is determined at a first time instant. At multiple time instants following the first time instant, multiple liquid hydrocarbon samples are obtained from the flowline. Each of the samples is processed as described earlier to determine a water content of liquid water in each of the liquid hydrocarbon samples. A water cut profile for the first liquid hydrocarbon sample and the multiple liquid hydrocarbon samples over a duration of time including the first time instant and the multiple time instants is determined.

An aspect combinable with any of the other aspects includes the following features. The solvent includes dry xylene.

Certain aspects of the subject matter described here can be implemented as a method. In step (a), a liquid hydrocarbon sample drawn from a flowline carrying the liquid hydrocarbon sample is mixed with a quantity of solvent. The liquid hydrocarbon sample includes liquid hydrocarbon and liquid water at a concentration greater than a water saturation level. The quantity of solvent is configured to reduce the liquid water to below the water saturation. In step (b), after mixing the liquid hydrocarbon sample with the solvent, a water content of the liquid water in the liquid hydrocarbon sample is determined.

An aspect combinable with any of the other aspects includes the following features. The solvent includes dry xylene.

An aspect combinable with any of the other aspects includes the following features. The liquid hydrocarbon sample is drawn from the flowline into a measurement cell.

An aspect combinable with any of the other aspects includes the following features. The quantity of solvent is flowed from a solvent storage tank into the measurement cell to mix the liquid hydrocarbon sample with the quantity of solvent.

An aspect combinable with any of the other aspects includes the following features. Before mixing the liquid hydrocarbon sample with the quantity of solvent, the solvent is dried to decrease water content in the solvent.

An aspect combinable with any of the other aspects includes the following features. Steps (a) and (b) are implemented at a first time instant. The steps are implemented at multiple time instants following the first time instant. Water contents are determined at the multiple time instants. The multiple water contents are plotted versus the multiple time instants to yield a water cut profile for the liquid hydrocarbon flowed through the flowline during the multiple time instants.

An aspect combinable with any of the other aspects includes the following features. The water content is transmitted to a computer system and displayed on a display device connected to the computer system.

An aspect combinable with any of the other aspects includes the following features. The mixture of the solvent and the liquid hydrocarbon sample is flowed to the flowline.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Certain crude oil processing refineries specify that the maximum water content of exported crude oil should be less than a water content threshold, for example, 0.2 weight percentage (wt. %). Water content at or below such threshold reduces processing cost for the refineries as well as the handling of contaminated water. If the water concentration in the liquid hydrocarbon is below water saturation level, then capacitance probes can be used to measure water content on the basis that the water concentration is homogeneous. However, if the water concentration is above saturation, then the assumption is invalid and the capacitance-based measurement techniques may be inaccurate. This disclosure describes adding a known amount of liquid hydrocarbon sample that includes liquid hydrocarbons and liquid water to a known amount of a solvent, for example, a low-dielectric solvent, such as dry xylene. In the context of this disclosure, a low-dielectric solvent is one that has a dielectric constant of less than five. More generally, a low-dielectric solvent is one that offers good compatibility with crude oil facilitating mixing and having low affinity with water to avoid large water uptake during storage that would be difficult to remove with a molecular sieve. The quantity of the solvent and the sample is chosen such that the water concentration in the sample will be below the water saturation level. The water cut in the mixture can then be measured, for example, using the capacitance-based measurement technique describes earlier. In the context of this disclosure, water saturation refers to a saturation point, that is, the threshold value, of water concentration above which water cannot be dissolved in the solvent anymore, and will be found in dispersed form of droplets or as a sediment within the solvent.

The online water cut measurement system described here can provide the ability to control the product streams closer to a refinery's specifications, for example, adjusting demulsifier and wash water flow rates. The techniques described here can be implemented for continuous, real-time water content measurements that can alert operators on changes in the water content of liquid hydrocarbons carried in flowlines. Such alerts can also enable the operators to change the process operation or to alert other operators of potential malfunction in upstream equipment. The water cut measurement techniques described here can provide accurate water cut data in an entire range of water concentration, that is, 0% to 100% range, more specifically, the 0% to 1% range. In addition, the techniques described here enable water cut measurement in liquid hydrocarbons with liquid water above water saturation levels.

Figure 1:
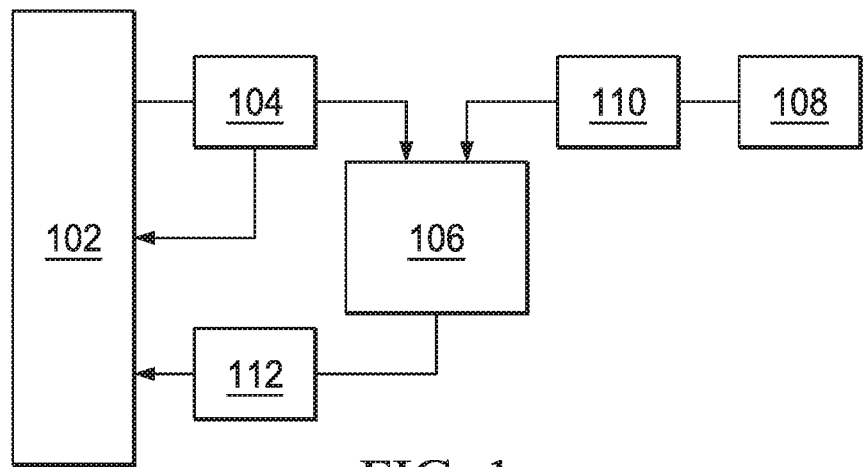
FIG. 1 is a schematic of a system for measuring water cut in a liquid hydrocarbon sample.

FIG. 1 is a schematic of a system for measuring water cut in a liquid hydrocarbon sample. The system includes a flowline 102 carrying liquid hydrocarbons. In some implementations, the flowline 102 can carry the liquid hydrocarbons produced through a wellbore (not shown). For example, the flowline 102 can run from a wellhead to a different location, for example, a gas oil separation plant (GOSP) or from a GOSP to a crude oil export terminal or stabilization plant. The liquid hydrocarbons flowed in the flowline 102 can include liquid water and, for example, liquid crude oil. A fast loop system 104 is fluidically coupled to the flowline 102 to obtain a liquid hydrocarbon sample from the flowline 102. The fast loop system 104 can be any fluidic system that includes an inlet and an outlet (for example, a drain) and that is fluidically coupled to a main line (here, the flowline 102). The fast loop system 104 can establish a continuous flow of fresh liquid hydrocarbon sample for the analysis described later. The fast loop system 104 can be configured to draw a desired quantity of the liquid hydrocarbon sample and a desired frequency at which the sample is to be drawn, for example, using a solenoid valve or an equivalent mechanism. In some implementations, the fast loop system 104 can be equipped with a flow metering system, a pump to allow reinjection into the flowline 102 or a filtering system (or a combination of any two or all three of them).

A measurement cell 106 is fluidically coupled to the fast loop system 104. A volume of a liquid hydrocarbon sample drawn from the flowline 102 by the fast loop system 104 is flowed to the measurement cell 106. The volume of the measurement cell 106 is determined by the volume of the liquid hydrocarbon sample used to measure the water cut. Excessively low volumes can lead to inaccuracies in measurement whereas excessively high volumes can increase the implementation cost. In some examples, the volume of the liquid hydrocarbon sample can be 10 milliliters (ml). In some implementations, the fast loop system 104 can include a flow pathway that returns the sample to the flowline 102 before the sample is flowed to the measurement cell 106. The fast loop system 104 allows conditioning the hydrocarbon sampled from the flowline 102, for example, in terms of pressure, flow rate and filtration requirements, and providing fresh sample to the measurement cell 106. In some implementations, the fast loop system 104 can provide the fresh sample at a frequency that matches the required measurement frequency, thereby avoiding product loss. Product not used for measurement is returned to the flowline 102.

The liquid hydrocarbon sample drawn into the measurement cell 106 includes liquid water at a concentration greater than the water saturation level. The concentration of the liquid water is decreased by adding a solvent, for example, a dielectric solvent such as xylene. In general, water and oil do not mix. However, dielectric solvents, such as xylene, can solubilize a minimal amount of water. Table 1 lists water solubility of certain solvents at a reference temperature. For example, xylene has a water solubility of 391 parts per million (ppm) at 25 centigrade (° C.). This means that each liter of dry xylene can solubilize up to 391 microliters (μl) of water. As water exceeds this concentration, it will drop out of the solution in the form of droplets and eventually form a sedimentation layer. In this disclosure the solvent to crude oil ratio is determined to meet the condition of solubility in the range of measurement of interest.

TABLE 1

BS&W stands for basic sediment and water and is a measure of free water, sediment and emulsion measured as a volume percentage of a production stream.

| Solvent | Water solubility @ 25° C. | | Max BS&W in crude oil vs crude-solvent ratio (volume) | | | | | | |
|---|---|---|---|---|---|---|---|---|---|
| | mol/l | ppm | 1 to 1 | 1 to 10 | 1 to 20 | 1 to 30 | 1 to 40 | 1 to 50 | 1 to 100 |
| Hexadecane | 0.0029 | 52 | 0.005% | 0.052% | 0.104% | 0.157% | 0.209% | 0.261% | 0.522% |
| Cyclohexane | 0.003 | 54 | 0.005% | 0.054% | 0.108% | 0.162% | 0.216% | 0.270% | 0.540% |
| CCl4 | 0.0087 | 157 | 0.016% | 0.157% | 0.313% | 0.470% | 0.627% | 0.784% | 1.567% |
| p-Xylene | 0.0217 | 391 | 0.039% | 0.391% | 0.782% | 1.173% | 1.564% | 1.955% | 3.909% |
| Toluene | 0.0265 | 477 | 0.048% | 0.477% | 0.955% | 1.432% | 1.910% | 2.387% | 4.774% |

TABLE 1-continued

BS&W stands for basic sediment and water and is a measure of free water, sediment and emulsion measured as a volume percentage of a production stream.

| Solvent | Water solubility @ 25° C. | | Max BS&W in crude oil vs crude-solvent ratio (volume) | | | | | | |
|---|---|---|---|---|---|---|---|---|---|
| | mol/l | ppm | 1 to 1 | 1 to 10 | 1 to 20 | 1 to 30 | 1 to 40 | 1 to 50 | 1 to 100 |
| Benzene | 0.0349 | 629 | 0.063% | 0.629% | 1.257% | 1.886% | 2.515% | 3.144% | 6.287% |
| Chlorobenzene | 0.029 | 522 | 0.052% | 0.522% | 1.045% | 1.567% | 2.090% | 2.612% | 5.224% |
| o-Dichlorobenzene | 0.024 | 432 | 0.043% | 0.432% | 0.865% | 1.297% | 1.729% | 2.162% | 4.324% |
| Chloroform | 0.0732 | 1319 | 0.132% | 1.319% | 2.637% | 3.956% | 5.275% | 6.593% | 13.19% |
| 1,2-Dichloroethane | 0.1262 | 2273 | 0.227% | 2.273% | 4.547% | 6.820% | 9.094% | 11.37% | 22.73% |
| 1,1,2,2-Tetrachloroethane | 0.101 | 1820 | 0.182% | 1.820% | 3.639% | 5.459% | 7.278% | 9.098% | 18.20% |

At higher temperatures than that reported in Table 1, it is expected that the solubility values will be larger, thereby extending the range of measurable water content. In one study, the solubility of water in p-xylene versus temperature at 689.5 kiloPascal (kPa) was measured. It was found that, for each incremental degree of temperature, the solubility increased by approximately 0.7% between 25° C. and 100° C. Therefore, a measurement at 60° C. rather than 25° C. would extend the water measurement range by 30%.

In some implementations, the solvent is stored in a solvent storage tank 108 that is fluidically coupled to the measurement cell 106. Depending on the application, the solvent in the solvent storage tank 108 can be xylene or another low dielectric solvent mentioned in Table 1. The solvent in the storage tank 108 is in a liquid state. The solvent can be flowed from the storage tank 108 to the measurement cell 106 using a pump (not shown). Alternatively, a pressure variation between the measurement cell 106 and the storage tank 108 can be used to draw the solvent from the storage tank 108 into the measurement cell 106. For example, pressure variation can be created by pressurizing the storage tank 108 with a dry gas (for example, nitrogen from a gas cylinder or dry instrument air from the plant). In this manner, a determined, for example, metered, quantity of the solvent can be flowed from the storage tank 108 to the measurement cell 106.

The quantity of the solvent drawn into the measurement cell 106 can be selected based on the volume of the liquid hydrocarbon sample drawn into the measurement cell 106 as well as the expected water cut measured by BS&W. For example, as shown in Table 1, to measure up to 0.782% water in a wet crude oil/xylene system, the crude oil/xylene ratio should be 1:20. For a measurement cell having a volume of 10.5 ml, this translates to 0.5 ml of crude oil and 10 ml of xylene, approximately.

In some implementations, the storage tank 108 and the measurement cell 106 are directly fluidically coupled, that is, through a pipeline and without any intermediate element. In general, the low dielectric solvent in the storage tank 108 is substantially water-free or, at minimum, has a water content below a water content threshold. In some implementations, the water content of the solvent can be further lowered by flowing the solvent through a drying chamber 110 prior to flowing the solvent to the measurement cell 106. For example, the drying chamber 110 can be fluidically coupled to the measurement cell 106 on one end and to the storage tank 108 on an another end. The solvent can be flowed from the storage tank 108 to the drying chamber 110. Drying can be implemented using silica gel, activated alumina, zeolites or a combination of them. For example, the drying chamber 110 can include or can be implemented as crystalline metal aluminosilicates having a three-dimensional interconnecting network of silica and alumina tetrahedra. Such implementations are effective to remove water from organic liquids.

In some implementations, the drying chamber 110 need not be a separate container in which the drying agents are disposed. Rather, the drying chamber 110 can be implemented as three Angstrom (3 A) to 5 A type molecular sieves disposed within the flow pathway, that is, the tubes or pipes, through which the solvent is flowed from the storage tank 108 to the measurement cell 110. Such molecular sieves can remove water from xylenes, since water molecules have 1.93 A size while xylenes have molecular size in the 6.5 A to 7.5 A range.

In some implementations, dry gas (for example, dry nitrogen or similar inert gas) is injected into the measurement cell 106 with the solvent. To create an overpressure and avoid moisture contamination in the solvent. Doing so can reduce the load on the drying agents and improve the dehydration process efficiency. In some implementations, a cartridge containing a molecular sieve or other drying agent can be located at an inlet of the storage tank 108 to avoid water entering the tank. In such implementations, the drying chamber 110 can function as a second cartridge to ensure complete dryness of the solvent before the solvent enters the measurement cell 106. Both, the cartridge at the inlet of the storage tank and the drying chamber 110, can be replaced periodically to ensure that water is collected efficiently. Certain types of cartridges (or the drying chamber) can be regenerated by heating above 120° C. under inert sweep to displace water from the molecular sieve.

After a quantity of the liquid hydrocarbon sample drawn from the flowline 102 and a quantity of the solvent drawn from the storage tank 108 are flowed to the measurement cell 106, the water cut of the mixture is measured. In some implementations, dry inert gas can be bubbled into the measurement cell 106 to facilitate mixing between the solvent and the sample. To do so, the measurement cell 106 is maintained at a particular temperature, for example, 40° C. In some implementations, the measurement cell 106 can be connected to a heater (not shown) or be positioned within a heating chamber (not shown) to maintain the measurement cell 106 at the particular temperature.

With the temperature of the measurement cell 106 maintained at the desired temperature, a water cut of the mixture within the measurement cell 106 is measured. The water cut can be measured by a capacitance type meter.

In some implementations, the measurement cell 106 is operatively coupled to a computer system (not shown). The computer system includes a computer-readable medium (for example, transitory or non-transitory computer-readable medium) storing instructions executable by one or more processors to perform operations. The operations include receiving water cut measurements from the measurement cell 106. For example, a sensor is installed inside the measurement cell 106 and can measure the water cut. The sensor is operatively coupled to the computer system and can transmit the water cut to the computer system. The computer system is operatively coupled to a display device (not shown). The computer system can display the water cut of a sample or generate and display a water cut profile (described later) of multiple samples in the display device. In some implementations, the water cut (or BS&W) can be displayed on the electronic enclosure of the water cut analyzer itself or sent remotely to a plant control room through a plant information (PI) system or similar data transmission system.

After the water cut of the sample has been measured, the sample is recovered from the measurement cell 106 and returned to the flowline 102. In some implementations, a sample recovery system 112 is fluidically coupled to the measurement cell 106 on one end and the flowline 102 on another end. In some implementations, the sample recovery system 112 includes a tank receiving the solvent-hydrocarbon mixture from the measurement cell 106. The sample recovery system 112 can be connected to a pump and emptied periodically either to a drain or into the flowline 102.

Figure 2:
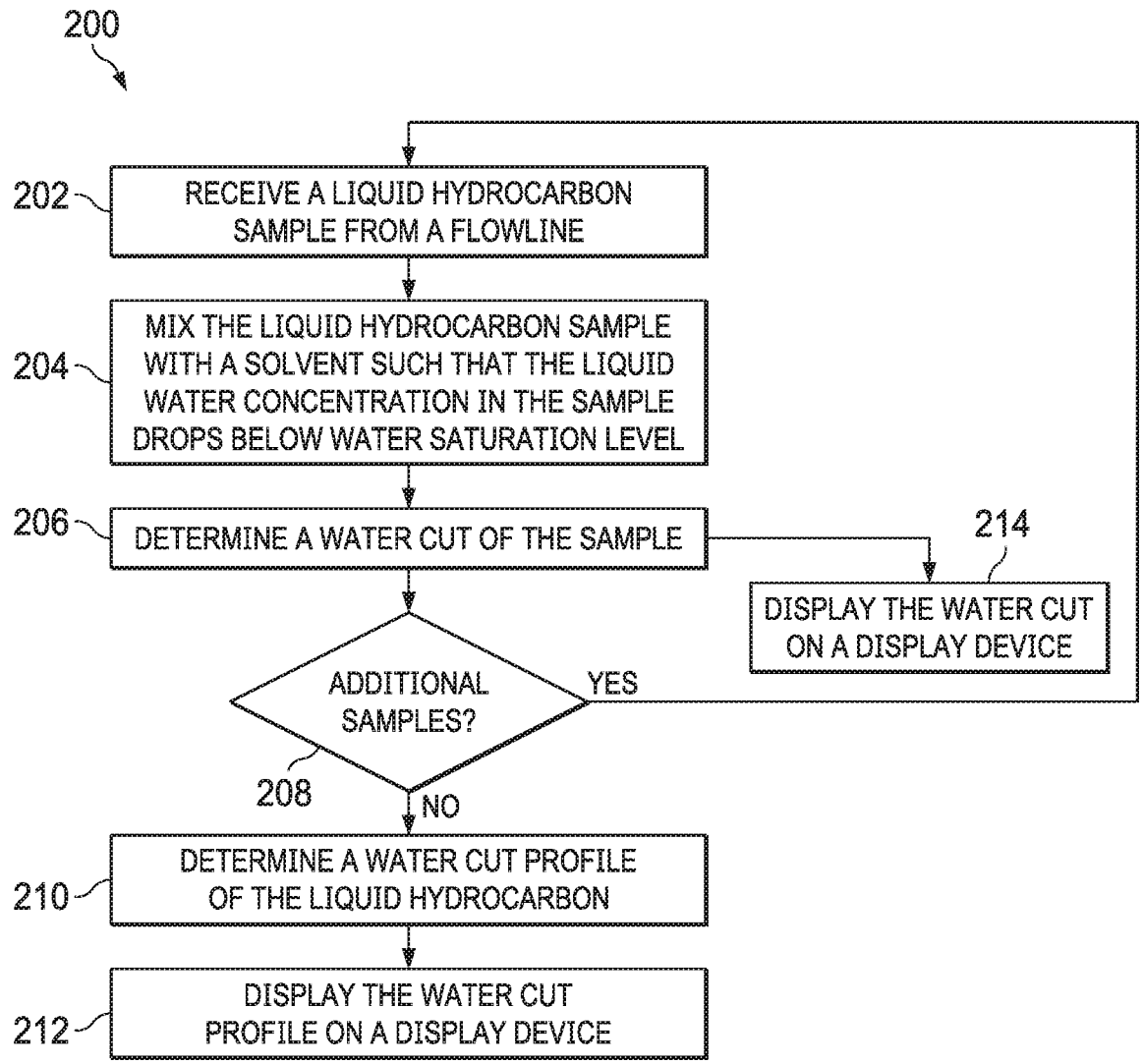
FIG. 2 is a flowchart of an example of a process for measuring water cut in a liquid hydrocarbon sample.

FIG. 2 is a flowchart of an example of a process 200 for measuring water cut in a liquid hydrocarbon sample. At 202, a liquid hydrocarbon sample is received from a flowline, for example, the flowline 102. At 204, the liquid hydrocarbon sample is mixed with a solvent, for example, from the solvent stored in the storage tank 108. The mixing is implemented, for example, in the measurement cell 106. At 206, a water cut of the sample is determined. At 214, the water cut is displayed, for example, on the display device of a computer system. At 208, it is determined if additional samples are to be measured for water content. If additional samples are to be measured (decision branch "YES"), then steps 202, 204 and 206 are repeated to determine the water cuts for multiple respective samples. In particular, each additional sample is drawn from the flowline at a respective time instant, and its water cut is measured. The frequency at which the different samples are drawn and water cut measured can depend upon the operation being performed or the process being controlled. For example, four samples can be drawn and measured periodically, that is, at equal time intervals, each hour. In this manner, water cuts of multiple samples drawn from the flowline over a duration that spans multiple time instants is obtained. If no additional samples remain (decision branch "NO"), then, at 210, a water cut profile of the liquid hydrocarbon is determined. The water cut profile is a plot of water cuts of the multiple samples versus the respective time instants at which the multiple samples were drawn from the flowline 102 or at which the water cut was measured for the multiple samples. The computer system can generate the water cut profile using any plot or graph generation software. At 214, the water cut is displayed on the display device.

In the implementation described with reference to FIGS. 1 and 2, the liquid hydrocarbon sample was drawn from the flowline 102 at a particular height measured from the bottom of the flowline 102. In such an implementation, the water cut of each sample or the water cut profile of multiple samples is representative of the water cut in the liquid hydrocarbon flowing through the flowline 102 at the measured height. In some implementations, the techniques described here can be implemented to determine water cut at different heights in a separation vessel. Recognizing that the water cut can be different at different heights within the vessel, multiple samples can be drawn from the vessel at different heights measured from the bottom of the vessel. By doing so, a water cut profile across a height of the vessel can be determined. Using the water cut or water cut profile (or both) measured as described in this disclosure, a control system can be programmed to create a relationship between water cut, that is, BS&W readings, and certain operations, for example, wash water flow rate, demulsifier flow rate, opening of recirculation valve, heating requirements in the presence of a heat exchanger or similar wellbore, flowline or plant operations. Off-spec crude oil can be segregated and sent to different tanks. In some implementations, a mixing element, for example, a static mixer, can be disposed in the flowline 102 and the hydrocarbon can be sampled downstream of the mixing element to ensure mixing of the hydrocarbons and obtaining a representative sample.

EXAMPLE

Figure 3:
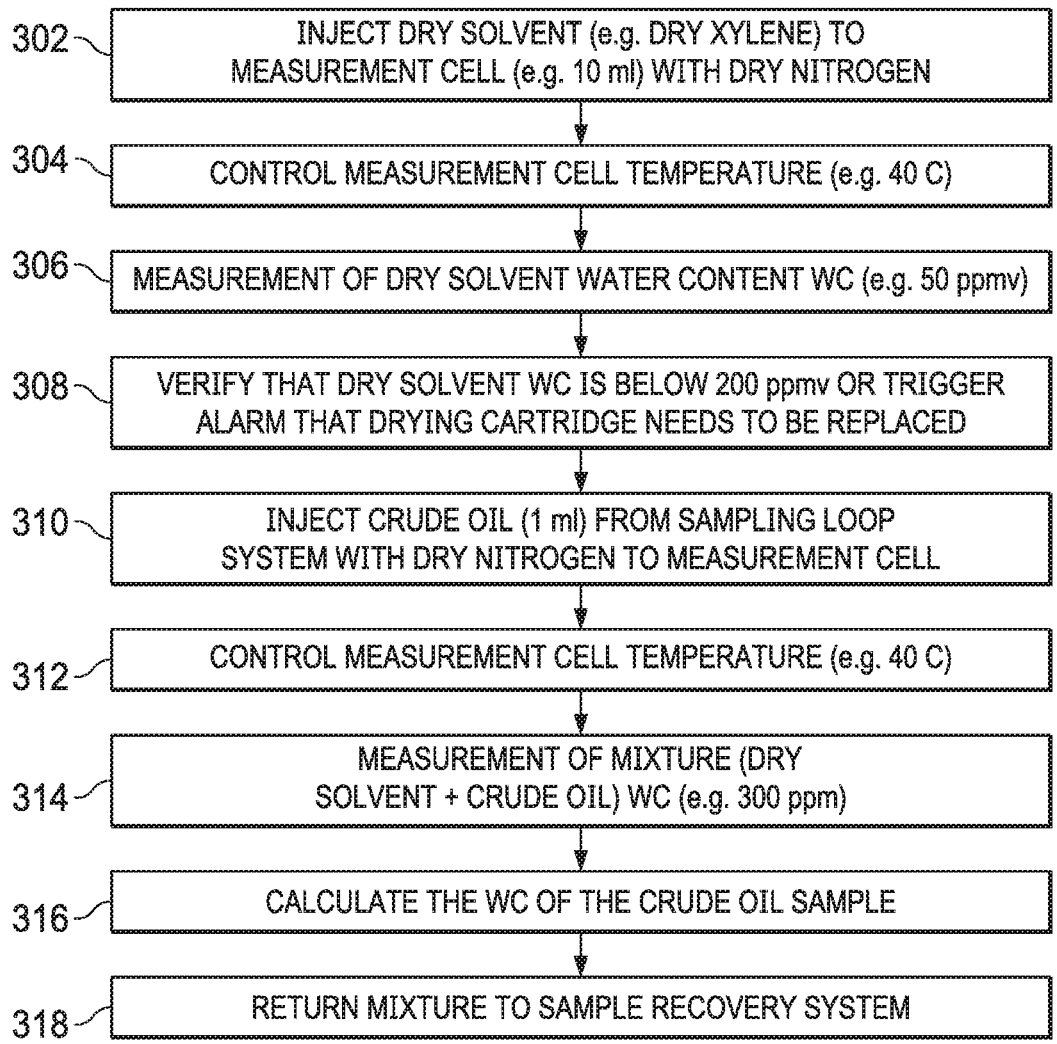
FIG. 3 is a description of an example of a process for measuring water cut in a liquid hydrocarbon sample.

FIG. 3 is a description of an example of a process for measuring water cut in a liquid hydrocarbon sample. At 302, dry xylene was injected into a 10 ml measurement cell with dry nitrogen. At 304, the temperature of the measurement cell was controlled at 40° C. At 306, water content in dry solvent was measured. The water content was found to be 50 parts per million by volume (ppmv). At 308, it was verified that the dry solvent water content was below a water content threshold of 200 ppmv. If the dry solvent water content had been greater than the water content threshold, then an alarm would have triggered requiring replacement of the solvent or the molecular sieve cartridge at the inlet of the solvent storage tank. At 310, 1 ml of crude oil was injected from the fast loop system with dry nitrogen into the measurement cell. At 312, a temperature of the measurement cell was maintained at 40° C. At 314, water content of the mixture of dry solvent and liquid hydrocarbon sample in the measurement cell was measured to be 300 ppm. At 316, the water cut of the liquid hydrocarbon sample was determined. In particular, the water cut of the crude oil sample was measured using the following formula:

$$\text{Liquid } HCWC = \frac{(mix.\ vol. \times mix.\ WC) - (\text{dry solvent } vol. \times \text{dry solvent } WC)}{\text{Liquid } HC \text{ volume}}$$

In the formula above, "mix. vol." stands for the volume of the mixture of the liquid hydrocarbon (HC) sample and the solvent and "mix. WC" stands for the water cut of the mixture. In this example, the liquid HC WC was 2800 ppm or 0.28%. At 318, the mixture was returned to the flowline through the sample recovery system.

In some implementations, the water cut measurement system described here can be calibrated. To do so, two samples can be drawn, either simultaneously or at different time instants. The samples can be diluted differently. For example, the first sample can be diluted at a 1:10 ratio, and the second sample can be diluted at a 1:20 ratio with a dilusion fluid, for example, the low-dielectric solvent. The water cut measurement can be implemented for both samples are described earlier. If the system operates as intended, then the water cut of the first sample will be twice that of the second sample. When similar calibration is implemented for multiple samples with a linear range of dilution ratios, the water cut profile for the samples will also be linear. Alternatively or in addition, processing two water samples of the same concentration (1:10 ratio or 1:20 ratio) in parallel allows solving a system of two equations with two unknowns (the original water contents in the hydrocarbons and the solvent), enabling measurement of the water content of the mixture components.

To summarize, the techniques described in this disclosure allow measuring the water content of water-saturated petroleum fluids that contain dispersed droplets. Implementing the techniques enables the water present in the form of droplets in the crude oil to be dissolved in a dry solvent, and hence to be easily measured as part of a homogeneous mixture. By varying the volume ratio of solvent and petroleum fluid, it is possible to cover a very wide range (for example, from 0% to 100%) of water concentrations in a petroleum fluid.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A method comprising:
   receiving a liquid hydrocarbon sample from a flowline carrying the liquid hydrocarbon, the liquid hydrocarbon sample comprising liquid hydrocarbon and liquid water at a concentration greater than a water saturation level;
   mixing the liquid hydrocarbon sample with a solvent, wherein the concentration of liquid water in a mixture of the solvent and the liquid hydrocarbon sample is below the water saturation level; and
   after mixing the liquid hydrocarbon sample with the solvent, determining a water content in the liquid hydrocarbon sample.

2. The method of claim 1, wherein receiving the liquid hydrocarbon sample comprises flowing the liquid hydrocarbon sample into a measurement cell.

3. The method of claim 2, further comprising controlling a temperature of the measurement cell to remain substantially at a temperature before mixing the liquid hydrocarbon sample with the solvent and during determining the water content of the liquid water in the liquid hydrocarbon sample.

4. The method of claim 3, wherein the temperature is 40° C.

5. The method of claim 2, wherein mixing the liquid hydrocarbon sample with a solvent comprises flowing the solvent into the measurement cell.

6. The method of claim 5, further comprising, before mixing the liquid hydrocarbon sample with the solvent:
   determining that a water content of the solvent is greater than a water content threshold; and
   responsive to determining that the water content of the solvent is greater than the water content threshold, transmitting an alarm signal to cease mixing the liquid hydrocarbon sample with the solvent.

7. The method of claim 1, further comprising:
   transmitting the water content to a computer system; and
   displaying the water content on a display device connected to the computer system.

8. The method of claim 1, further comprising flowing the mixture of the solvent and the liquid hydrocarbon sample to the flowline.

9. The method of claim 1, wherein the liquid hydrocarbon sample is a first liquid hydrocarbon sample, the solvent is a first solvent, the water content is a first water content, wherein the first water content is determined at a first time instant, wherein the method further comprises, at a respective plurality of time instants following the first time instant:
   receiving a respective plurality of liquid hydrocarbon sample from the flowline, each of the liquid hydrocarbon samples comprising liquid hydrocarbon and liquid water at a respective concentration greater than a water saturation level;
   mixing each of the liquid hydrocarbon samples with the solvent;
   after mixing each of the liquid hydrocarbon samples with the solvent, determining a water content of liquid water in each of the liquid hydrocarbon samples; and
   developing a water cut profile for the first liquid hydrocarbon sample and the plurality of liquid hydrocarbon samples over a duration comprising the first time instant and the plurality of time instants.

10. The method of claim 1, wherein the solvent comprises dry xylene.

11. A method comprising:
   (a) mixing a liquid hydrocarbon sample drawn from a flowline carrying the liquid hydrocarbon with a quantity of solvent, the liquid hydrocarbon sample comprising liquid hydrocarbon and liquid water at a concentration greater than a water saturation level, the quantity of solvent configured to reduce the liquid water to below the water saturation; and
   (b) after mixing the liquid hydrocarbon sample with the solvent, determining a water content of the liquid water in the liquid hydrocarbon sample.

12. The method of claim 11, wherein the solvent comprises dry xylene.

13. The method 11, further comprising drawing the liquid hydrocarbon sample from the flowline into a measurement cell.

14. The method of claim 13, wherein mixing the liquid hydrocarbon sample with the quantity of solvent comprises flowing the quantity of solvent from a solvent storage tank into the measurement cell.

15. The method of claim 11, further comprising, before mixing the liquid hydrocarbon sample with the quantity of solvent, drying the solvent to decrease water content in the solvent.

16. The method of claim 11, wherein steps (a) and (b) are implemented at a first time instant, the method further comprising:
   implementing steps (a) and (b) at a plurality of time instants following the first time instant;
   determining a plurality of water contents at the plurality of time instants; and
   plotting the plurality of water contents versus the plurality of time instants to yield a water cut profile for the liquid hydrocarbon flowed through the flowline during the plurality of time instants.

17. The method of claim 11, further comprising:
   transmitting the water content to a computer system; and
   displaying the water content on a display device connected to the computer system.

18. The method of claim 11, further comprising flowing the mixture of the solvent and the liquid hydrocarbon sample to the flowline.

\* \* \* \* \*